United States Patent [19]

Rabinowitz

[11] Patent Number: 4,997,489

[45] Date of Patent: Mar. 5, 1991

[54] EXTRACTION OF PRODUCTS FROM ALMOND FRUIT

[76] Inventor: Israel N. Rabinowitz, 2534 Foothill Rd., Santa Barbara, Calif. 93105

[21] Appl. No.: 349,019

[22] Filed: May 8, 1989

[51] Int. Cl.⁵ .................. C13D 1/00; C13D 3/14; C07C 35/14; C07C 51/42
[52] U.S. Cl. .................. 127/43; 127/46.2; 127/46.3; 127/55; 127/45; 210/660; 210/681; 568/868; 568/872; 568/833; 562/580; 562/582; 562/584; 562/593
[58] Field of Search .................. 127/43, 46.2, 46.3, 127/55; 426/271; 568/868, 872, 833; 562/580, 582, 584, 593; 210/660, 681

[56] References Cited

U.S. PATENT DOCUMENTS 4,482,761 11/1984 Chao et al. .................. 127/46.2
4,544,778 10/1985 Chao et al. .................. 127/46.2

FOREIGN PATENT DOCUMENTS 0056663 4/1983 Japan .................. 426/271

OTHER PUBLICATIONS

*Journal of Agri. and Food Chem.*, "The Carbohydrate Composition of Almond Hulls", vol. 18 (1970), pp. 950-951.

*Primary Examiner*—Chung K. Pak
*Attorney, Agent, or Firm*—Donald D. Mon

[57] ABSTRACT

The invention relates to a process for recovering sugar, sugar alcohol and organic acids comprising citric, malic and quinic acids from a juice extracted from almond hulls. Residues from the extraction is also recovered.

2 Claims, 1 Drawing Sheet

EXTRACTION OF PRODUCTS FROM ALMOND FRUIT

FIELD OF THE INVENTION

This invention relates to the extraction of useful products from almond fruit, and in particular from almond hulls.

BACKGROUND OF THE INVENTION

The chemical composition of almond hulls has been the source of previous comment in the literature. For example, in U.S. Pat. No. 4,482,761 to Chao the presence of inositol and other sugar alcohols, and of sugars. The water extract of almond hulls disclosed. In this patent, the use the molecular sieves to separate these useful compounds is also disclosed. Sequeira et al, "The Carbohydrate Composition of Almond Hulls", J. Agri. Food Chem. Vol. 18 (1970) pp 950-951 is another discussion of the composition of almond hulls.

Almond hulls are a natural product forming a part of the almond fruit itself. They are produced as a by-product of the processes of producing the most-utilized part of the almond fruit, namely the stone.

It is not a matter of common knowledge, nor well understood in industry and commerce, that the sources of the almond nut is a druit tree. The sweet almond (Prusnus amygdalus, Amygdalus communis) is specifically a stone fruit (drupe), in which the fleshy part, the mesocarp or "hull", is derived from the ovary of the flower and surrounds the shell (endocarp), teguement (thin papery covering), and finally the stone or "nut" itself. Almond trees are currently cultivated commerically solely for the value of the edible nut, or in the case of the bitter almond, for the flavoring extracts expressed from the otherwise inedible nut. Almonds are most closely related to other stone fruit, such as peach (Prunus persica), apricot (P. armeniaca) and plum (P. domestica, P. instititia, et al.) in which the stone is indeed a stone in the common understanding and is not edible, whereas the mesocarp (not referred to as a "hull") is, and it forms the basis for the commerical exploitation of these fruit.

The process of growth, maturation, absission, and senescense of the almond fruit, is such that early in its growth stage the "hull" can be eaten by humans processing pleasing taste, texture, and nutritional value, whereas by maturation and thereafter the hull is leathery in texture and astringent to the taste, although its nutritional value has actually increased. Unfortunately, this increase in nutritional values is accompanied by the presence of other chemical components which can temporarily sicken a human.

As recently as thirty years ago, the nutritional value of the almond hull was not sufficiently understood, and after harvest of the nuts, in California, the hulls were either used for landfill, burned for removal, or perhaps burned for their fuel value. Starting about thirty years ago, agricultural scientists in California introduced and pioneered the use of almond hulls in animal feed, primarily cattle, in which animals the chemical components troublesome to humans do not upset the animals, and nutritional value is obtained at low cost.

The inventor in this instant patent application has observed that several chemical components of almond hulls, present after fruit maturation, have individual and important commerical values, and has devised a commerical process to separate and purity each of them, leaving very little to waste. For example, prior to the introduction of the use of hulls for animal feed, almond hulls had a negative or zero commerical value. Currently, for feed usage, almond hulls have a value averaging about $50/ton. The process invention described herein can raise the value of the almond hull (as separate components) to approximately $800/ton.

The success of this process depends upon understanding the physiology and biochemistry of the mature almond fruit and the precise application of commerical separation science techniques to selectively extract components of value without destruction or loss of any of the components.

It is an object of this invention to produce organic acids such as citric, malic, and quinic acids from this source. The instant inventor is unaware of disclosure in the literature of the present of these compounds in almond hulls.

BRIEF DESCRIPTION OF THE INVENTION

According to this invention, almond hulls are soaked in water to dissolve their water soluable components, including organic acids. Thereafter the hulls are separated from the solution (the "juice") and are discard or further processed.

The juice obtained from this extraction contains sugars, sugar alcohols, and, among other substances, various organic acids, including citric, malic and quinic. If desired, the sugars and sugar alcohols such as sorbitol, inositol and mannitol, can be removed as taught in the Chao patent and the remainder treated according to this invention, or the entire juice may be treated. In either case, the solution containing the organic acids is passed through an ion exculsion column to remove the mixed organic acids, which may be treated as the ultimate product, or may thereafter be separated from one another by conventional procedures to provide the individual acids.

DETAILED DESCRIPTION OF THE INVENTION

Figure 1:
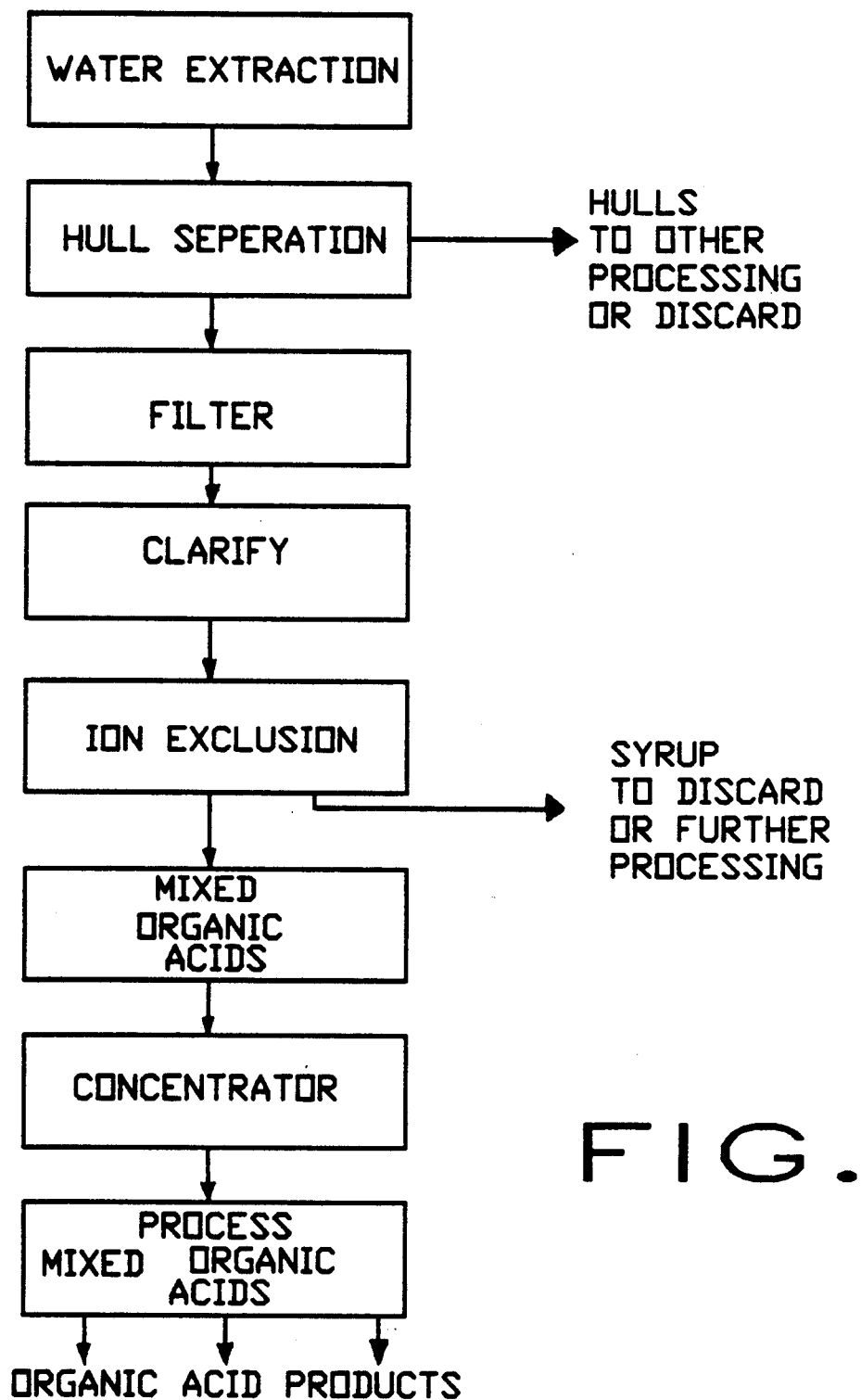
FIG. 1 is a flow chart showing the presently preferred embodiment of the invention.

Almond hulls for this process will usually reach the process as dry or slightly moist large- sized particles. The compounds and compositions of interest to this invention are mostly contained inside the cell walls. When the hulls are soaked, the sugars and sugar alcohols can readily pass through the cell wall, and do so. The tannins, however, do not readily pass through the cells walls. Therefore, when tannins are sought as a product, it is best practice to do as little violence to the cells as possible. Also, gentle treatment at this time results in less tannins entering the juice, which will have to be removed by clarification procedures. For these reasons, the hulls will preferably not be ground or pulverized before or during the soak procedure.

Water and hulls are added to any suitable vessel, and the hulls are soaked in order to dissolve the sugars and sugar alcohols, which enter into solution. Best results are obtained by the use of classical counter current water extraction technique, wherein water enters the soaking process where the extracted hulls leave, and the solution leaves the process where the hulls enter. Counter current extraction is not essential to the invention. A straight soak procedure is suitable, but better results are attained with counter current techniques. The extraction is best accomplished at temperatures between about 50 and 70 degrees C.

Hull separation is conveniently a screening or coarse filtration process, preferably without pressing, because pressing may release tannins into the juice by rupturing the cell walls. However, if maximum juice is the objective, a gentle pressing can be made.

The juice is provided to a clarifier such as a plate and frame filter, or a multiple step liming precipitation procedure. The resulting extract is a sweet syrup product principally containing fructose, glucose, and sugar alcohols including inositol and sorbitol. It may be concentrated by evaporation or diluted with water to the desired degree of concentration or sweetness. The organic acids are separated from the concentrated almond fruit syrup either before or after the sugar alcohols is separated via molecular sieves. It is preferable to perform the separation prior to the sugar alcohol separation by passing the concentrated fruit juice over an organic ion exchange column, and collecting a fraction of mixed organic acids which is effected by a process known as ion exclusion. The exchange media also desalts simultaneously by well-known ion exchange mechanisms. The organic acid solution is then concentrated to a solid content suitable for sale, and/or further partitioned into individual organic acid products, separated by preferential distillation, precipitation, or ion exchange and evaporative concentration.

This invention is not be limited by the embodiment shown in the drawings and described in the description, which is given by way of example and not of limitation, but only in accordance with the scope of the appended claims.

I claim:

1. The process of extraction of products from almond hulls, comprising:
   a. soaking almond hulls in water to extract soluble substances therefrom the product juice and hull residue, and separating said juice from said residue; and
   b. passing said juice through an ion exclusion column to recover organic acids comprising citric, malic and quinic acids therefrom.

2. A process according to claim 1 in which said juice is passed through a molecular sieve before being passed through said ion exculsion column to recover at least some sugar or sugar alcohol.

* * * * *